(12) United States Patent
Iketaki et al.

(10) Patent No.: US 7,304,315 B2
(45) Date of Patent: Dec. 4, 2007

(54) THREE DIMENSIONAL ANALYZING DEVICE

(75) Inventors: Yoshinori Iketaki, Tokyo (JP); Masaaki Fujii, Yokohama (JP); Takeshi Watanabe, Yamato (JP); Takashige Omatsu, Yokohama (JP); Kimihisa Yamamoto, Tokyo (JP); Toshio Suzuki, Chiba (JP)

(73) Assignees: Japan Science & Technology Agency, Kawaguchi-shi (JP); Olympus Corporation, Tokyo (JP); Nippon Roper Co., Ltd., Tokyo (JP)

( * ) Notice: Subject to any disclaimer, the term of this patent is extended or adjusted under 35 U.S.C. 154(b) by 0 days.

(21) Appl. No.: 11/404,248

(22) Filed: Apr. 13, 2006

(65) Prior Publication Data

US 2006/0290924 A1   Dec. 28, 2006

Related U.S. Application Data

(63) Continuation of application No. PCT/JP2004/014105, filed on Sep. 27, 2004.

(30) Foreign Application Priority Data

Oct. 15, 2003   (JP) .............................. 2003-355327

(51) Int. Cl.
*G01N 21/64* (2006.01)
*G01J 3/00* (2006.01)

(52) U.S. Cl. ................... 250/461.2; 356/300

(58) Field of Classification Search ............ 250/461.2, 250/458.1, 234, 339.01, 459.1, 492.2

See application file for complete search history.

(56) References Cited

U.S. PATENT DOCUMENTS

| | | | | |
|---|---|---|---|---|
| 5,485,530 A | * | 1/1996 | Lakowicz et al. | 382/191 |
| 5,731,588 A | * | 3/1998 | Hell et al. | 250/458.1 |
| 5,952,668 A | * | 9/1999 | Baer | 250/492.2 |
| 6,184,535 B1 | * | 2/2001 | Kashima et al. | 250/459.1 |
| 6,633,432 B2 | | 10/2003 | Iketaki | |

(Continued)

FOREIGN PATENT DOCUMENTS

JP    2001-100102 A    4/2001

(Continued)

OTHER PUBLICATIONS

Article entitled "Fluorescence Correlation Spectroscopy in DNA Analysis", by Masataka Kinjo, Journal of The Japanese Society for Precision Engineering, vol. 65, No. 2, 1999, pp. 175-180.

(Continued)

*Primary Examiner*—David Porta
*Assistant Examiner*—Faye Boosalis
(74) *Attorney, Agent, or Firm*—Frishauf, Holtz, Goodman & Chick, P.C.

(57) ABSTRACT

A three-dimensional analyzing device includes a first beam source for generating a first beam, a second beam source for generating a second beam, an optical system for spatially overlapping the first and second beams at least partly and irradiating the beams onto a specimen to three-dimensionally confine a photoactive region in a specimen, and a photo acceptance element for accepting a response light emitted from the photoactive region. Preferably, the device further includes an operation unit for calculating a correlation function of a response light in the time domain based on the output of the photo acceptance element to analyze a desired physical value of the specimen.

24 Claims, 13 Drawing Sheets

U.S. PATENT DOCUMENTS 6,667,830 B1    12/2003   Iketaki et al.
6,844,963 B2    1/2005   Iketaki et al.
7,098,447 B2 *   8/2006   Moellmann ................ 250/234

FOREIGN PATENT DOCUMENTS

| | | |
|---|---|---|
| JP | 2001-272343 A | 10/2001 |
| JP | 2001-272346 A | 10/2001 |
| JP | 2002-062261 A | 2/2002 |
| JP | 2002062261 A * | 2/2002 |

OTHER PUBLICATIONS

Article entitled "Excited Singlet-State Absorption in Dyes and Their Effect on Dye Lasers", by E. Sahar and D. Treves, IEEE, Journal of Quantum Electronics, QE-13, No. 12, Dec. 1977, pp. 962-967.

* cited by examiner

THREE DIMENSIONAL ANALYZING DEVICE

CROSS-REFERENCE TO RELATED APPLICATIONS

The present application is a Continuing Application based on International Application PCT/JP2004/014105 filed on Sep. 27, 2004, which, in turn, claims the priority from Japanese Patent Application No. 2003-355327 filed on Oct. 15, 2003, the entire disclosure of these earlier applications being herein incorporated by reference.

TECHNICAL FIELD

The present invention relates to a three-dimensional analyzing device particularly for analyzing a physical value associated with the size or number of molecules contained in a specimen, based on an optical response generated from a three-dimensionally confined observation region of a dyed specimen.

BACKGROUND OF THE INVENTION

As an analyzing method applicable for such a three-dimensional analyzing device, there is known a fluorescence correlation method as disclosed, for example, in a non-patent document: "*Fluorescence Correlation Spectroscopy in DNA Analysis*", authored by Masataka KINJO, Journal of The Japan Society for Precision Engineering, Vol. 65, No. 2, 1999, pp. 175-180. The fluorescence correlation method has long been used in analysis on a diffusive motion such as Brownian movement of particles, in which, as shown in a principle diagram of FIG. 13, physical values associated with the size or number of fluorescence molecules are analyzed based on a fluorescence correlation function of the amplitude and duration of fluctuation, which is obtained by irradiating a narrow laser beam as an exciting beam to a dilute solution of fluorescence molecules, and measuring a fluorescence intensity in an observation region exposed to the laser beam for a long time. Since the fluorescence intensity is proportional to the number N of fluorescence molecules included in the observation region, the intensity of fluctuation in terms of S/N can be expressed as $(1/N)^{1/2}$.

In such a fluorescence correlation method, the correlation time $\tau 0$, i.e., the length of time during which the fluorescence correlation function as a physical value decreases by half, can be expressed as the following formula (1):

$$\tau 0 = \frac{W^2}{4D} \qquad (1)$$

where D is a translational diffusion coefficient of the fluorescence molecule, and W is a beam radius of the laser beam when the intensity distribution function thereof in its radial direction follows the Gaussian distribution. In a physical sense, the correlation time $\tau 0$ corresponds to the length of time during which fluorescence molecules pass across the laser beam by diffusion.

In the fluorescence correlation method, the fluorescence fluctuation is generally measured with an output current f(t) of a photoelectron multiplier that receives the fluorescence, wherein the output current f(t) is proportional to the fluorescence quantity when the radius of the laser beam is not extremely large. The fluorescence correlation function is equivalent a correlation function $G(\tau)$ of the output current f(t) with respect to time. The fluorescence correlation function $G(\tau)$ can be expressed as the following formula (2), which can be simplified as the following formula (3) when the laser beam intensity substantially follows the Gaussian distribution.

$$G(\tau) = \frac{\int_0^\infty f(t)f(t+\tau)dt}{\int_0^\infty f(t)f(t)dt} \qquad (2)$$

$$G(\tau) = \frac{1}{N} \cdot \frac{1}{1+\tau/\tau_0} \qquad (3)$$

As explained above, the fluorescence correlation method makes it possible to measure, basically in the same principle, any physical value from which a translational diffusion coefficient can be obtained, provided that the physical value is a thermodynamic value that gives a fluorescence fluctuation. For example, a fluorescence fluctuation can be observed when fluorescence molecules pass across the laser beam by flowage thereof. If a fluorescence molecule is bound with another molecule in a chemical reaction, for example, a molecule velocity can be observed as a fluctuation. In other words, the development of the chemical reaction can be known in a real time manner. In addition, a rotational movement of a molecule can also be measured with ellipsometry.

Further, the number of molecules included in the observation region can be measured directly, based on the intensity of the fluorescence correlation function $G(\tau)$. More specifically, a fluctuation f(t) during a certain measuring time long enough for an expected fluctuation to be completed is measured, which is then used for obtaining a correlation function with the formula (2). Generally, a CW (continuous wave) argon laser or krypton laser is used as an exciting beam source for analyzing a fluorescence correlation of a pigment molecule. A representative system for the fluorescence correlation analysis used in the prior art is shown in FIG. 15.

In the system shown in FIG. 15, an argon laser 51 is used as an exciting beam source, from which a laser beam is emitted and transmitted through a beam splitter 52, to be collected by a lens 53 and irradiated to a specimen solution 54 containing fluorescence molecules. The fluorescence in the specimen solution 54 is collimated by the lens 53 and reflected by the beam splitter 52, to be collected by a lens 55. The collected fluorescence passes through a pinhole 56 to be received by a detector 57, such as a photoelectron multiplier or CCD. The output of the detector 57 is amplified by a preamplifier 58, converted by an analog/digital (A/D) converter 59 into digital data, and then inputted to an operational equipment 60 comprising a computer etc., for calculating the correlation function $G(\tau)$.

The system of the type shown in FIG. 15 is also disclosed in the non-patent document identified above.

According to various experimental studies conducted by the inventors, however, it has been found from practical viewpoint that the above-mentioned system for a fluorescence correlation analysis as used in the prior art is still to be improved in the following points.

As the fluorescence correlation method is based on detection of fluctuation, the number of the fluorescence molecules is preferably as small as possible, particularly one molecule if possible. However, the region exposed to a beam inducing a fluorescence has a lower limit in size, i.e., a diffraction limit that is defined by the numerical aperture (NA) of the lens 53 and the wavelength λ of the beam, as expressed by the following formula (4). Thus, as the absolute quantity of fluorescence molecules increases, the region exposed to the beam should be narrowed down correspondingly, to reduce the number of fluorescence molecules passing across the observation region.

$$W = 1.22 \frac{\lambda}{NA} \quad (4)$$

Therefore, even when the lens 53 comprises an immersion lens of NA=1.4 and a laser beam of λ=500 nm is used as the exciting beam in FIG. 15, for example, a focusing radius W of the laser beam is 436 nm at the lowest. Moreover, the size in the depth direction of the beam coincides with the very thickness of the specimen solution 54. Thus, in carrying out a measurement in practice, it is required to extremely lessen the density of fluorescence molecules contained in the specimen solution 54 to be analyzed, which is a significant obstacle to the practical utility.

In order to limit the size of the observation region in the depth direction of the beam, a pinhole 56 is generally provided at the confocal position for cutting the fluorescence emitted from a region outside the focal plane. However, even with the provision of such a pinhole, the resolution in the depth direction nevertheless remains on the order of several micrometers. Further, the positioning of the pinhole 56 is delicate, with the result that the fluorescence to be observed is also cut in many instances.

For the reasons explained above, it has been difficult to apply the fluorescence correlation method to a concentrated solution, besides that a high three-dimensional spatial resolution cannot be expected, either.

DISCLOSURE OF THE INVENTION

In view of the circumstances described above, it is an object of the present invention to provide a three-dimensional analyzing device that is capable of accurately calculating a correlation function of an optical response by three-dimensionally confining an observation region, even if a specimen solution contains concentrated optical responsive molecules.

In order to achieve the above-mentioned object, a first aspect of the present invention resides in a three-dimensional analyzing device comprising:

a first beam source for generating a first beam;

a second beam source for generating a second beam having a different wavelength than said first beam;

an optical system for three-dimensionally confining a photoactive region in a specimen by irradiating said first beam and said second beam so that said first beam spatially overlaps said second beam at least partly, and utilizing a fluorescence inhibition effect caused thereby; and a light-sensitive element for receiving an response light emitted from said photoactive region.

A second aspect of the present invention resides in the three-dimensional analyzing device according to the first aspect, further comprising an operation unit for analyzing a desired physical value of said specimen by calculating a correlation function of said response light in the time domain, based on an output of said light-sensitive element.

A third aspect of the present invention resides in the three-dimensional analyzing device according to the first aspect, wherein: said specimen includes a molecule having at least three electronic states including a ground state; said first beam has such a wavelength as to make a transition of said molecule from the ground state to a first excited state; and said second beam has such a wavelength as to make a transition of said molecule from the first excited state to a second excited state having a higher energy level.

A fourth aspect of the present invention resides in the three-dimensional analyzing device according to the third aspect, wherein the wavelength of said second beam ranges in a wavelength spectrum of an induced emission of said specimen.

A fifth aspect of the present invention resides in the three-dimensional analyzing device according to the fourth aspect, wherein the wavelength of said second beam ranges is within such a wavelength spectrum as to inhibit an emission of said response light from the spatial region exposed to both said first and second beams.

A sixth aspect of the present invention resides in the three-dimensional analyzing device according to the first aspect, wherein said response light is a fluorescence.

A seventh aspect of the present invention resides in the three-dimensional analyzing device according to the first aspect, further comprising a first irradiation intensity controlling unit and a second irradiation intensity controlling unit for separately controlling intensities of said first and second beams irradiated to said specimen.

An eighth aspect of the present invention resides in the three-dimensional analyzing device according to the first aspect, wherein at least said second beam is a coherent beam.

A ninth aspect of the present invention resides in the three-dimensional analyzing device according to the first aspect, further comprising a spatial modulation unit for subjecting said second beam to a spatial modulation.

A tenth aspect of the present invention resides in the three-dimensional analyzing device according to the ninth aspect, wherein said spatial modulation means comprises a spatial phase modulation unit.

An eleventh aspect of the present invention resides in the three-dimensional analyzing device according to the tenth aspect, wherein said spatial phase modulation unit comprises such a phase distribution region as to produce a spatially discontinuous phase difference of $(2m+1)\pi$ in said second beam over a radial direction from an optical axis in a pupil of said optical system, where m is an integer.

A twelfth aspect of the present invention resides in the three-dimensional analyzing device according to the eleventh aspect, wherein said spatial phase modulation unit comprises a phase plate.

A thirteenth aspect of the present invention resides in the three-dimensional analyzing device according to the twelfth aspect, wherein said phase distribution region comprises an optical thin film for producing said phase difference on an optical substrate.

A fourteenth aspect of the present invention resides in the three-dimensional analyzing device according to the thirteenth aspect, wherein said phase distribution region comprises at least three concentric circular sections, each pair of neighboring sections producing said different phase difference of $(2m+1)\pi$.

A fifteenth aspect of the present invention resides in the three-dimensional analyzing device according to the thirteenth aspect, wherein said phase distribution region comprises two sections in shapes of concentric circles.

A sixteenth aspect of the present invention resides in the three-dimensional analyzing device according to the fifteenth aspect, wherein a radius of a beam flux of said second beam transmitting through said phase plate is $2^{1/2} \cdot r$, where r is a radius of the inner section of said two sections.

A seventeenth aspect of the present invention resides in the three-dimensional analyzing device according to the sixteenth aspect, wherein the center of said inner section corresponds to the center of curvature of the beam flux radius of said second beam.

An eighteenth aspect of the present invention resides in the three-dimensional analyzing device according to the twelfth aspect, wherein said phase distribution region comprises an etching section on the optical substrate for producing said phase difference.

A nineteenth aspect of the present invention resides in the three-dimensional analyzing device according to the eighteenth aspect, wherein said phase distribution region comprises at least three concentric circular sections, each pair of neighboring sections producing said different phase difference of $(2m+1)\pi$.

A twentieth aspect of the present invention resides in the three-dimensional analyzing device according to the eighteenth aspect, wherein said phase distribution region comprises two sections in shapes of concentric circles.

A twenty-first aspect of the present invention resides in the three-dimensional analyzing device according to the twentieth aspect, wherein a radius of a beam flux of said second beam transmitting through said phase plate is $2^{1/2} \cdot r$, where r is a radius of the inner section of said two sections, A twenty-second aspect of the present invention resides in the three-dimensional analyzing device according to the twenty-first aspect, wherein the center of said inner section corresponds to the center of curvature of the beam flux radius of said second beam.

A twenty-third aspect of the present invention resides in the three-dimensional analyzing device according to the first aspect, further comprising a positioning mechanism for positioning with a precision of $0.2\lambda/NA$ a concentration point on said specimen of said first and second beams in said optical system, where $\lambda$ is a wavelength of said second beam and NA is a numerical aperture of said optical system.

A twenty-fourth aspect of the present invention resides in the three-dimensional analyzing device according to the first aspect, further comprising a two-dimensional scanning unit for two-dimensionally scanning said first and second beams to said specimen in a plane perpendicular to the optical axis of said optical system.

BEST MODE FOR CARRYING OUT THE INVENTION

The three-dimensional analyzing device according to the present invention will be described below, with reference to a preferred embodiment.

The three-dimensional analyzing device according to the illustrated embodiment is based on a fluorescence inhibition effect arising from a double resonance absorbance process induced by irradiating two beams having different wavelengths to a molecule having three quantum states including a ground state.

Figure 1:
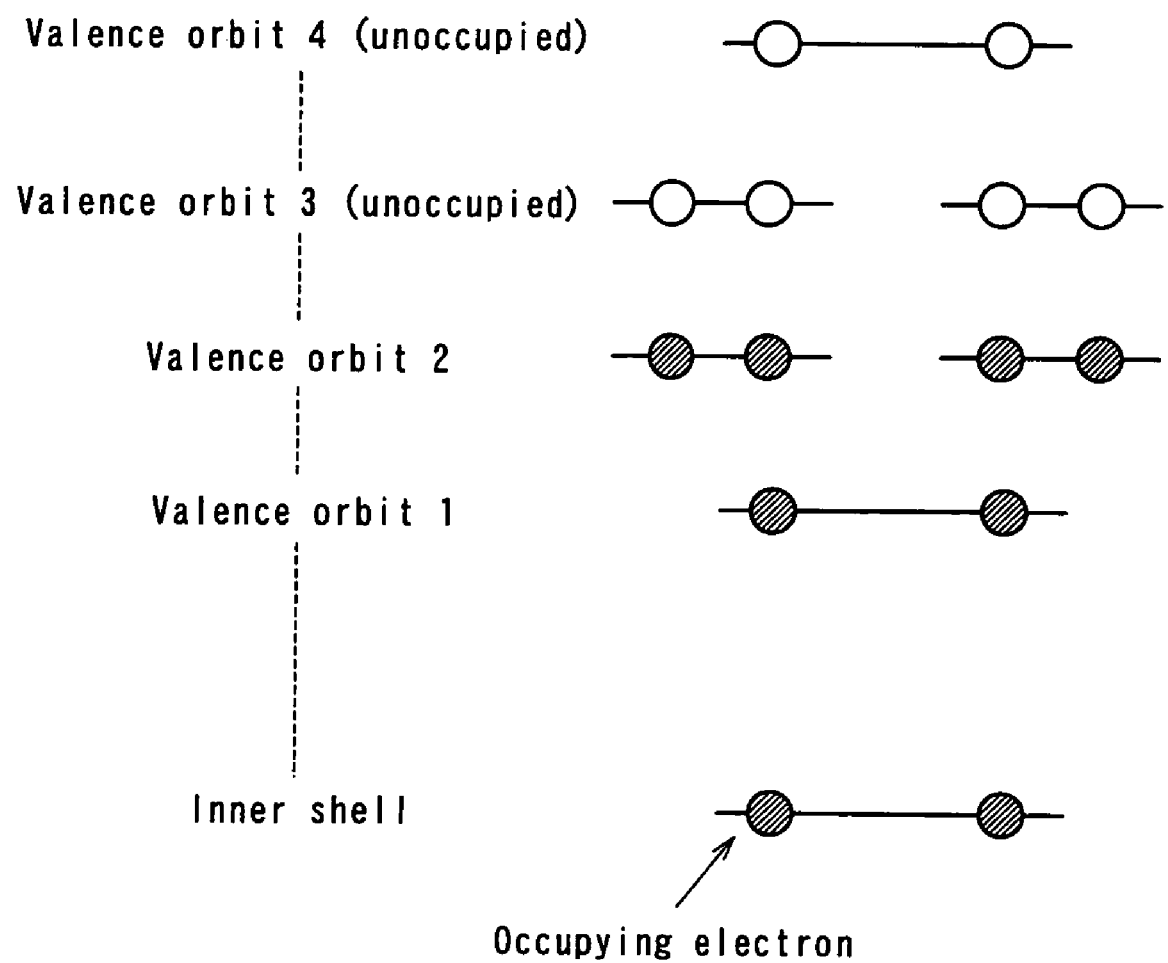
FIG. 1 is a conceptual diagram showing an electron structure of a valence orbit of a molecule included in a specimen.
Figure 2:
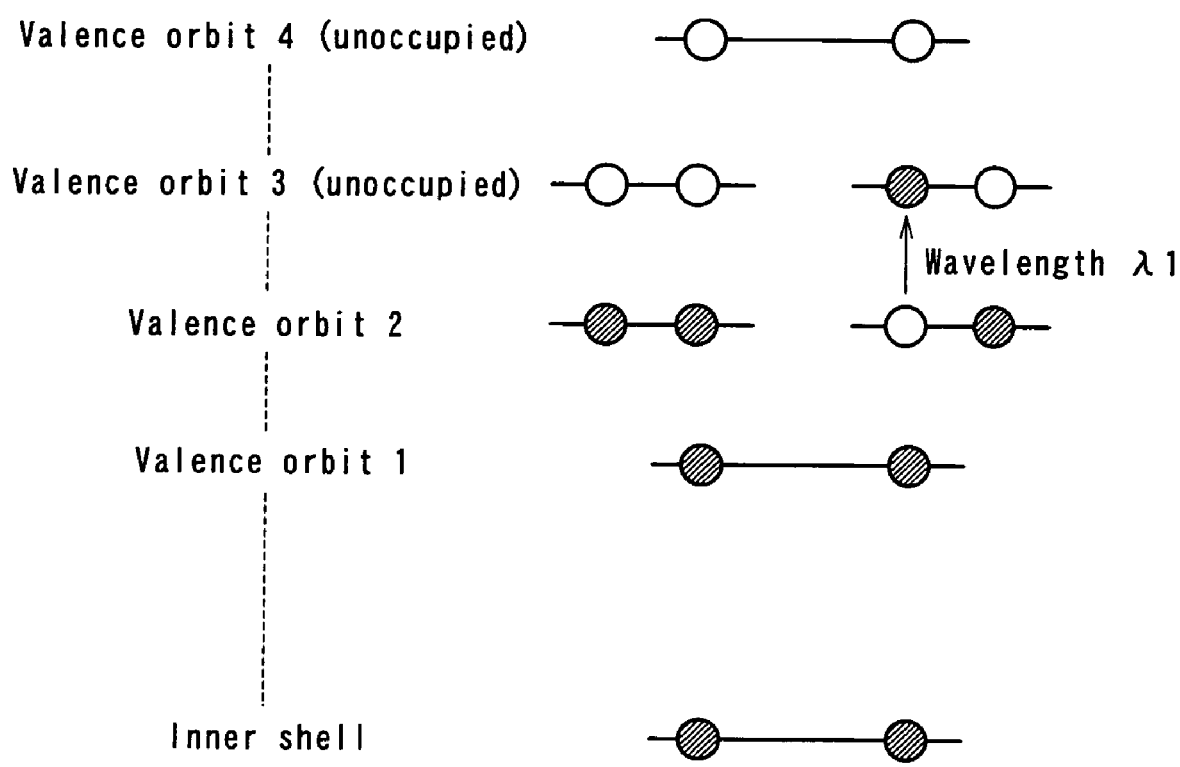
FIG. 2 is a conceptual diagram showing a first electronically-excited state of the molecule in FIG. 1.
Figure 3:
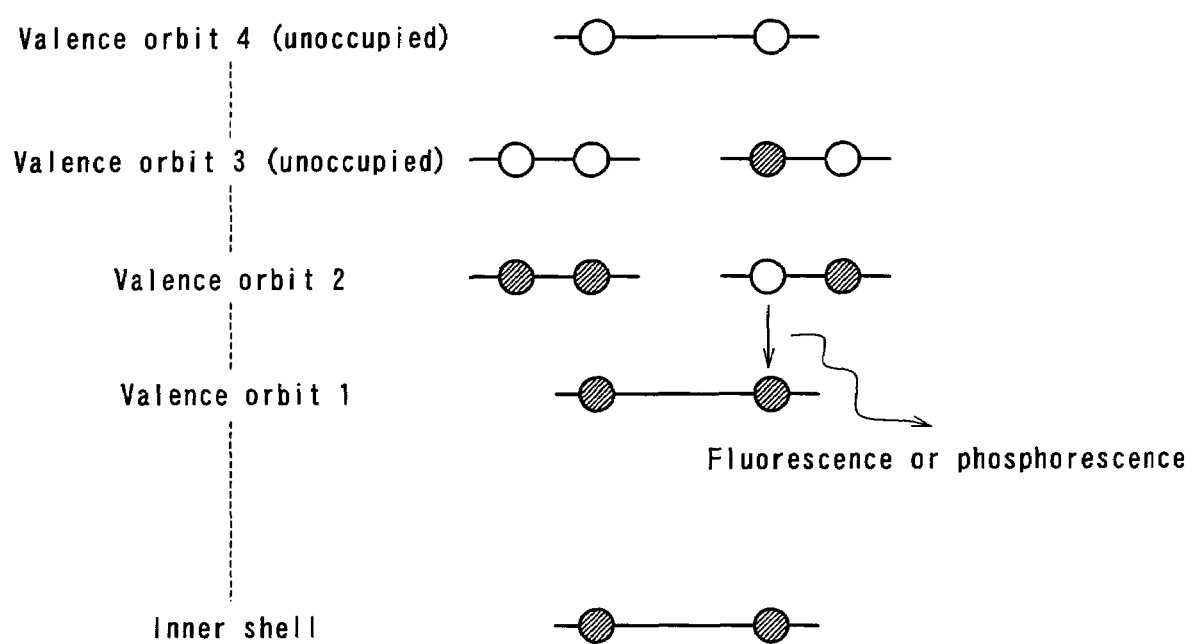
FIG. 3 is a conceptual diagram showing a step of returning to the ground state from the first electronically-excited state.
Figure 4:
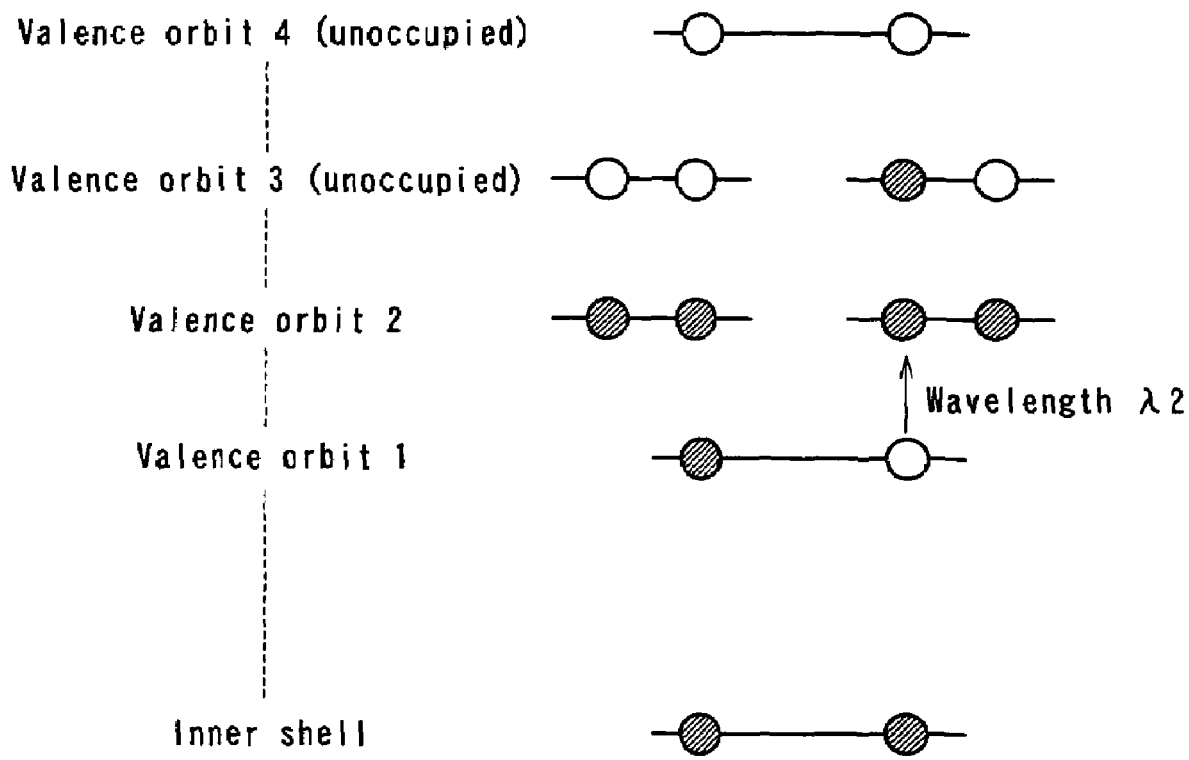
FIG. 4 is a conceptual diagram showing a second electronically-excited state of the molecule.
Figure 5:
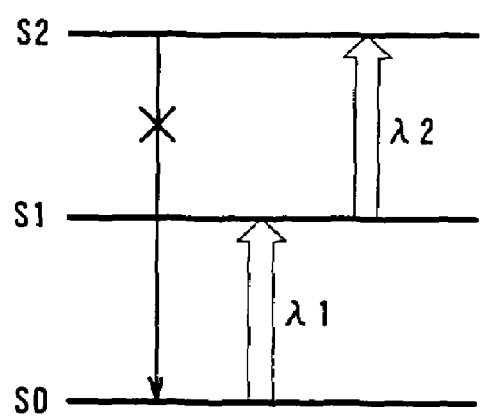
FIG. 5 is a conceptual diagram showing a step of returning to the ground state from the second electronically-excited state.

The above fluorescence inhibition effect is explained first of all. In FIG. 1 representing an electron structure of a valence orbit of a molecule, a beam having a wavelength $\lambda 1$ is irradiated to a molecule in the ground state (S0 state) as shown in FIG. 1 to excite the molecule to a first electronically-excited state (S1 state). In this electronically-excited state, the molecule usually emits a fluorescence or phosphorescence to return to the ground state as shown in FIG. 3. However, if the molecule is excited with another beam having a wavelength $\lambda 2$ in the same manner, the molecule is brought to a second electronically-excited state (S2 state) as shown in FIG. 4. In this electronically-excited state, many molecules emit the excitation energy as heat to the outside medium, instead of emitting a fluorescence, so as to return to the ground state as shown in FIG. 5.

There has been recently proposed a fluorescence microscope utilizing a fluorescence inhibition effect arising from a double resonance absorbance process, to provide a spatial resolution higher than a diffraction limit (see, for example, Japanese Patent Application Laid-open Publication JP 2001-100102 A1).

Figure 6:
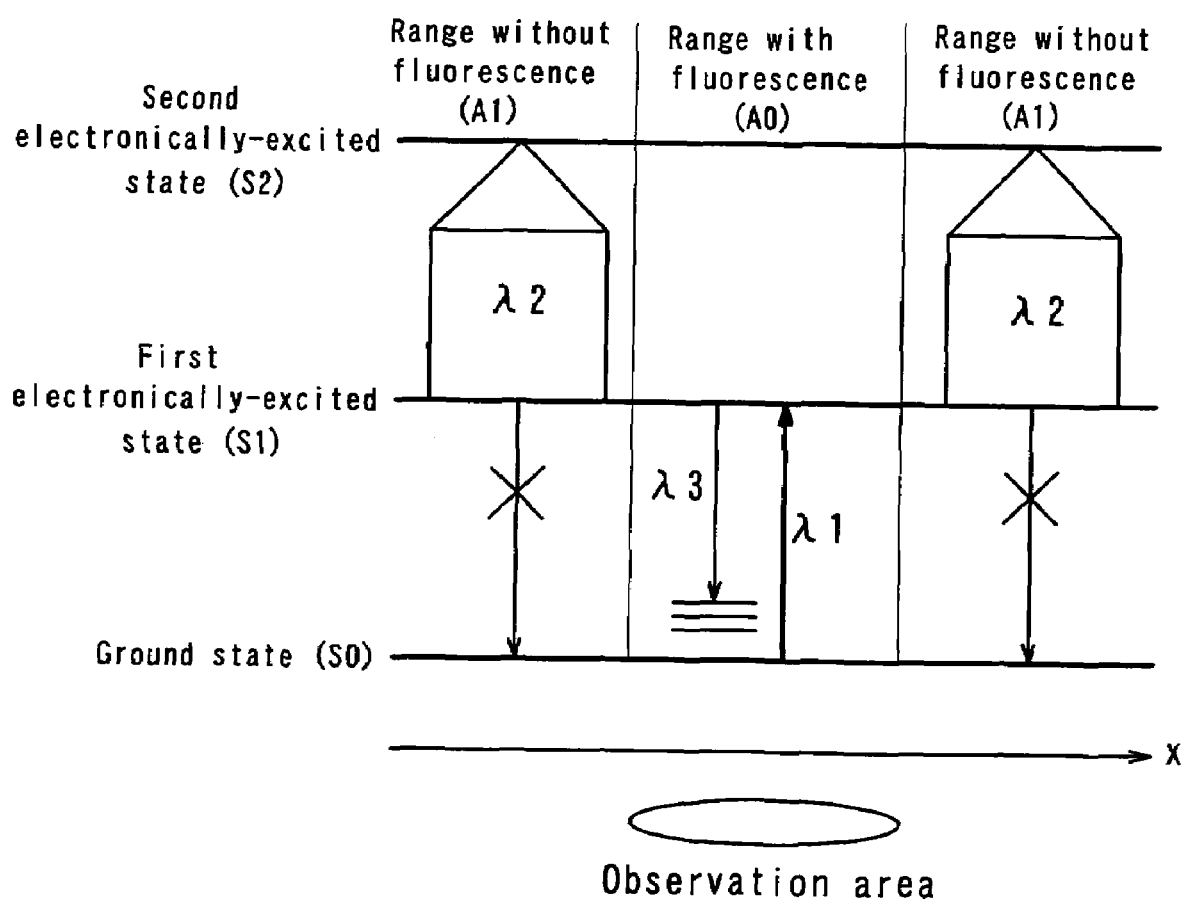
FIG. 6 is a conceptual diagram explaining a double resonance absorbance process in a molecule.

As to a molecule having the above-mentioned optical property, a phenomenon of significant interest can be observed. FIG. 6 is a conceptual diagram explaining a double resonance absorbance process in the same manner as FIG. 5, where a horizontal axis X represents a stretch of spatial distance, which is divided into a spatial region A1 exposed to the beam of the wavelength $\lambda 2$, and a spatial region A0 not exposed to the beam of the wavelength $\lambda 2$.

In FIG. 6, a number of molecules in the S1 state are generated by a beam excitation of the wavelength λ1 within the spatial region A0, whereby a fluorescence of a wavelength λ3 from the spatial region A0 can be observed. In the spatial region A1, on the other hand, being exposed to the beam of the wavelength λ2, most molecules in the S1 state are immediately excited to the S2 state of higher energy level, so that there exist no molecules in the S1 state any longer. Such a phenomenon has been confirmed with respect to some molecules. Thus, the fluorescence of the wavelength λ3 being completely extinguished and there being no fluorescence from the S2 state from the beginning, a fluorescence is completely inhibited in the spatial region A1 (the fluorescence inhibition effect), so that the fluorescence is emitted only from the spatial region A0.

From the viewpoint of the microscope application field, this has an extremely important meaning. Namely, with a conventional microscope such as a scanning laser microscope, a laser beam is focused into a microbeam by a focusing lens to scan on a specimen. The size of the microbeam is limited to the diffraction limit determined by the numerical aperture of the focusing lens and the wavelength. Therefore, a higher spatial resolution is theoretically unachievable.

In contrast, in the case of FIG. 6, the beams of the wavelength λ1 and the wavelength λ2 are optimally overlapped and the fluorescence region is confined by irradiation of the beam of the wavelength λ2. Thus, with reference to the range exposed to the beam of the wavelength λ1, for example, the range of fluorescence can be made narrower than the diffraction limit determined by the numerical aperture of the concentration lens and the wavelength, thereby making it possible to improve the spatial resolution (hereinafter, the beam of the wavelength λ1 and the beam of the wavelength λ2 are referred to as a "pumping beam" and an "erasing beam" respectively). Consequently, by utilizing the above principle, it is possible to realize a super-high resolution microscope, for instance a fluorescence microscope.

Figure 7:
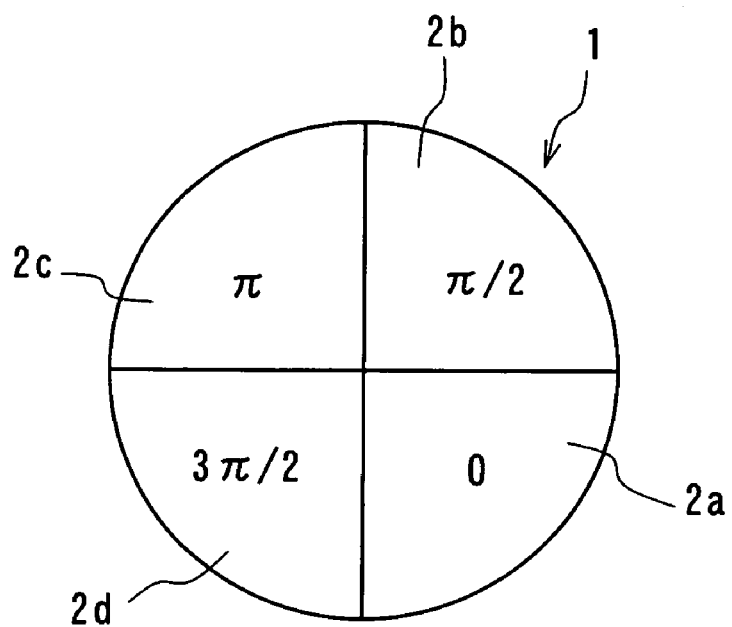
FIG. 7 is a diagram showing an example of a phase plate that can be used in a three-dimensional analyzing device according to the present invention.

As shown in FIG. 6, in order to effectively concentrate the erasing beam so that there are an exposure region and non-exposure region, for example, there is known a method which utilizes a phase plate 1 for a spatial modulation of the erasing beam, as shown in FIG. 7. The phase plate 1 comprises an optical substrate and an optical thin film deposited thereon, which is configured so that a passing erasing beam has an inverted phase with respect to a position of the optical axis symmetry. More specifically, the passing beam has four independent sections 2a-2d, and the phase in each section differs in steps of ¼ with respect to the wavelength of the erasing beam. By focusing a beam having passed through the phase plate 1, the electrical field is canceled out on the optical axis to generate an erasing beam of a hollow shape.

In the present embodiment, the above-mentioned super-high resolution microscope technology is applied so that the fluorescence in the selected spatial region is erased to measure only the fluorescence emitted from a three-dimensionally confined observation region, and to thereby obtain a fluorescence correlation function thereof.

Figure 8:
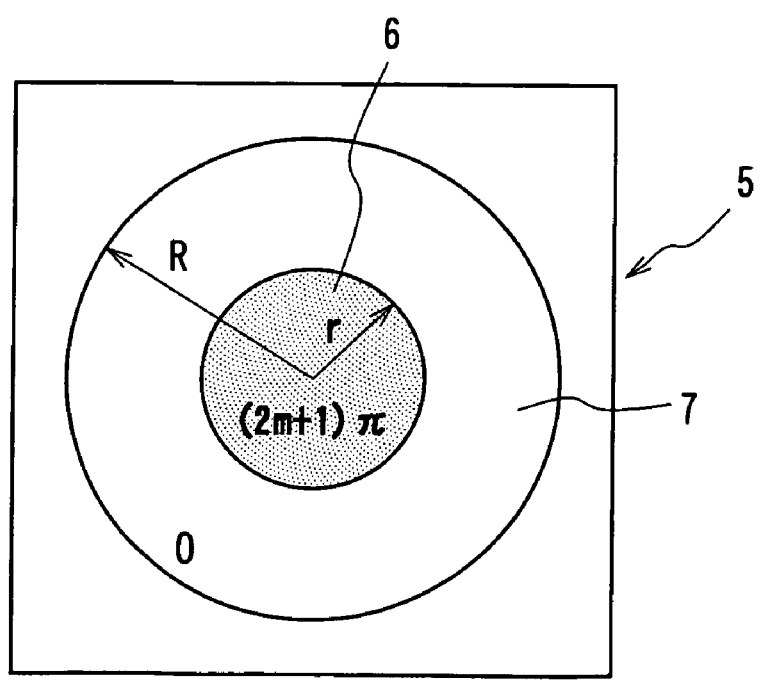
FIG. 8 is a diagram showing another example of the phase plate that can be used in the device.

Instead of the phase plate 1 shown in FIG. 7 for controlling the phase so that the beam intensity of the erasing beam on the optical axis of the erasing beam is constantly zero, as shown in FIG. 8, there may be used a phase plate 5 for shifting the phase by $(2m+1)\pi$ of a beam in a circular region 6 of a radius r having its center on the optical axis and being concentric with an optical pupil having a radius R (r<R) to transmit the erasing beam so that the exposure to the erasing beam is inhibited only in a region around the focused point, wherein the symbol m represents any integer. Usually, the phase difference can be produced by etching or thin film deposition.

Figure 9:
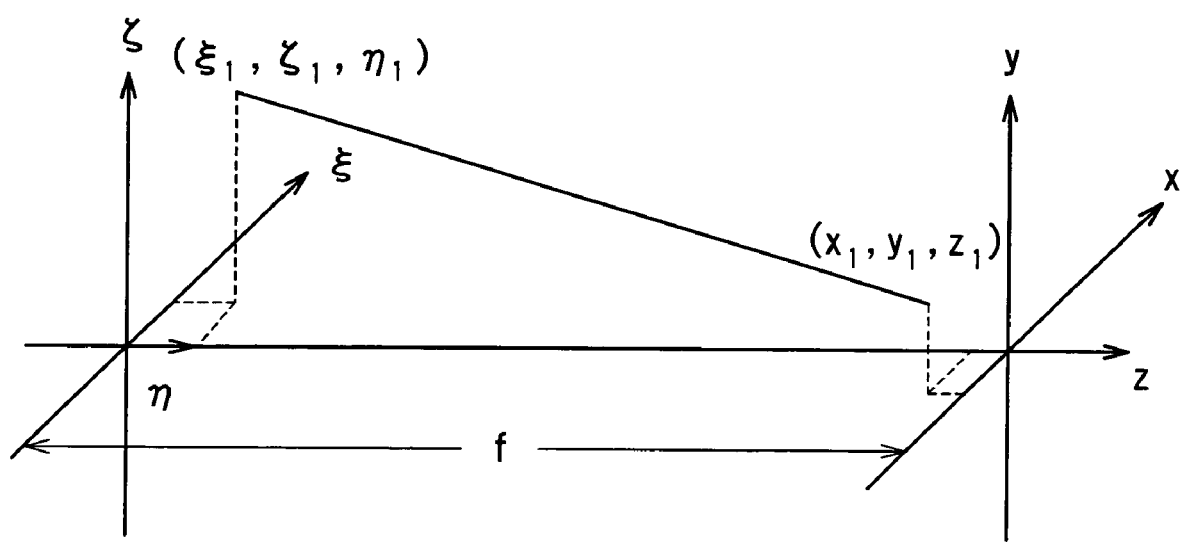
FIG. 9 is a diagram for explaining a beam concentration pattern observed when the beam is subjected to a phase modulation.

Generally, if a beam of a wavelength λ entering into a concentration lens is subjected to a phase modulation of $f(\xi, \zeta, \eta)$, according to a wave optics theory, the beam concentration pattern is expressed as the following formula (5) using a coordination system of FIG. 9:

$$I(x, y, z) = \left| \int_{NA} \int e^{-if(\xi,\zeta,\eta)} e^{-i\frac{2\pi}{\lambda}V(x,y,z,\xi,\zeta,\eta)} d\xi d\zeta \right|^2 \quad (5)$$

wherein, $$V(x, y, z, \xi, \zeta, \eta) = \sqrt{(x-\xi)^2 + (y-\zeta)^2 + (z-\eta)^2} - \sqrt{x^2 + y^2 + (z-f)^2}$$

and $$\xi^2 + \zeta^2 + (f-\eta)^2 = f^2$$

In the above formula (5), f represents a focal length of an optical system, (x, y, z) a point of observation, and $(\xi, \zeta, \eta)$ integral valuables. The integral range is a numerical aperture NA corresponding to the entirety of the pupil in an optical system. In particular, if a phase distribution as shown in FIG. 8 is provided on the surface of the pupil $(\xi, \zeta)$ of the erasing beam, the formula (5) represents a beam concentration pattern subjected to a spatial modulation. More specifically, the phase difference of $(2m+1)\pi$ is provided in a region of $\xi^2 + \zeta^2 < r^2$, while no phase difference is provided in a region of $r^2 \leq \xi^2 + \zeta^2 < R^2$, where the radius of the pupil is represented by R. Here, as a relative phase difference matters, the situation can be dealt with in the same manner even if no phase difference is provided in the region of $\xi^2 + \zeta^2 < r^2$ and the phase difference of $\pm(2m+1)\pi$ is provided in the region of $r^2 \leq \xi^2 + \zeta^2 < R^2$.

When an erasing beam with a uniform intensity distribution enters into the phase plate 5 having a radius R as shown in FIG. 8 and the transmitted beam is focused with a focusing lens, the intensity of the erasing beam in proximity of the focal point (0, 0, 0) is zero in the case of $R = 2^{1/2} \cdot r$. This is because, in FIG. 8, the inner circular region 6 and the outer annular region 7 have the same surface area and inverted phases, and the intensity of the erasing beam thus becomes zero at the focal point where all the rays of the beam are focused at a single point.

Figure 10:
FIG. 10 is a diagram showing a result of simulation of an intensity distribution around the focal point of a beam having been subjected to a phase modulation by the phase plate shown in FIG. 8.

On the other hand, the intensity of the erasing beam increases at positions spaced more or less from the focal point. Specifically, FIG. 10 illustrates the result of simulation of an intensity distribution around the focal point by using the formula (5), showing that there is formed a spheroidal region without beam intensity, having dimensions, in units of λ/NA, of about λ/NA in the x-y plane (focal plane) and about 0.2×λ/NA in the x-z plane or y-z plane (in the direction of the optical axis).

Using an erasing beam having a wavelength λ of 500 nm and a concentration lens having a numerical aperture NA of 1.4, for example, there is formed an ultramicroscopic spatial region that is not exposed to the beam, which is of a shape of spheroid having dimensions of approximately 357 nm in the x-y plane and approximately 72 nm in the x-z or y-z plane and a volume of approximately $5.9 \times 10^{-15}$ cm$^3$.

Accordingly, when a pumping beam is overlapped at the focal point with an erasing beam having such a spatial region, the region of a molecule fluorescence can be confined into the above-mentioned ultramicroscopic spatial region due to the fluorescence inhibition effect. Furthermore, by optimizing the intensity of the erasing beam as disclosed in Japanese Patent Application Laid-open Publication JP 2001-100102 A2, the region with the fluorescence inhibition effect can be made narrower than $\lambda/NA$, thereby making it possible to refine the effective observation region, for example, to one sixth of the region not exposed to the erasing beam, and to produce a super resolution microscopy observation region having a two-digit smaller volume.

Through various experimental studies, the inventors found that, if the spatial region of the erasing beam is suitably controlled and the erasing beam and the pumping beam are overlapped at the focal point of a focusing lens, the fluorescence emitting region can be confined into a super resolution microscopy spatial region. The inventors further found that, if the method of irradiating the erasing beam and the pumping beam is applied to the fluorescence correlation method, the behavior of a single molecule within a ultramicroscopic space of the observation region can be analyzed with high accuracy. Such findings resulted in the conception of the present invention.

Thus, use of the three-dimensional analyzing device according to the present invention enables a unimolecular analysis to be achieved even in a concentrated solution, which has been impossible with the prior art. Moreover, with an optimization of the erasing beam intensity, the observation region can further be confined into a smaller space than $1.0 \times 10^{-14}$ cm$^3$. In particular, with the three-dimensional analyzing device of the present invention having a three-dimensional resolution inclusive of the optical axis direction, a spatial filter of a small radius for achieving a spatial resolution in the optical axis direction is not required, which has been needed for the conventional system; only a spatial filter with a relatively large radius sufficient for inhibiting a stray beam needs to be provided in front of the detector, thereby significantly facilitating the adjustment of the optical system.

The three-dimensional analyzing device according to the present embodiment will be further explained below with reference to FIG. 11 and FIG. 12.

Figure 11:
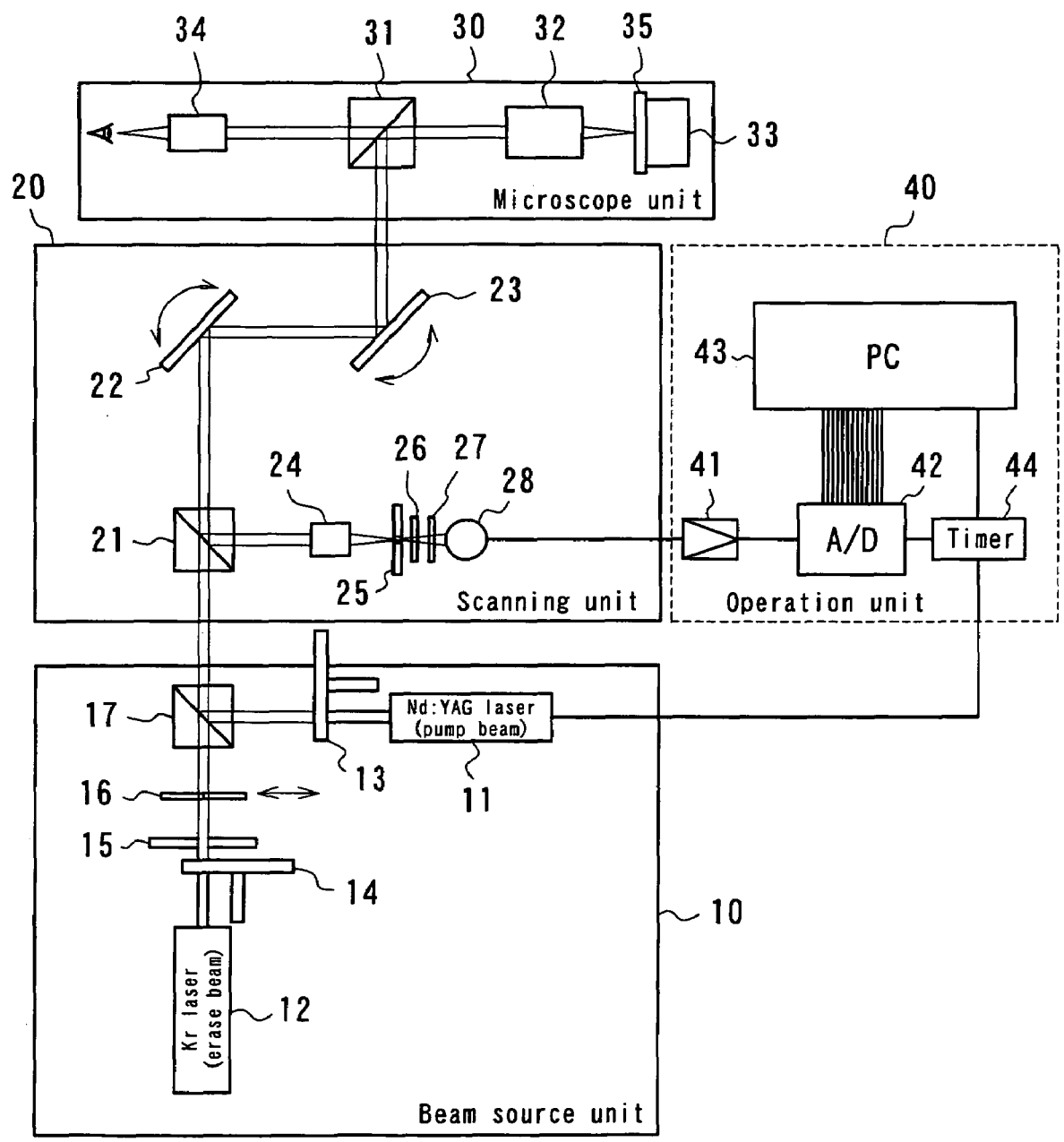
FIG. 11 is a schematic diagram of the three-dimensional analyzing device according to one embodiment of the present invention.
Figure 12A:
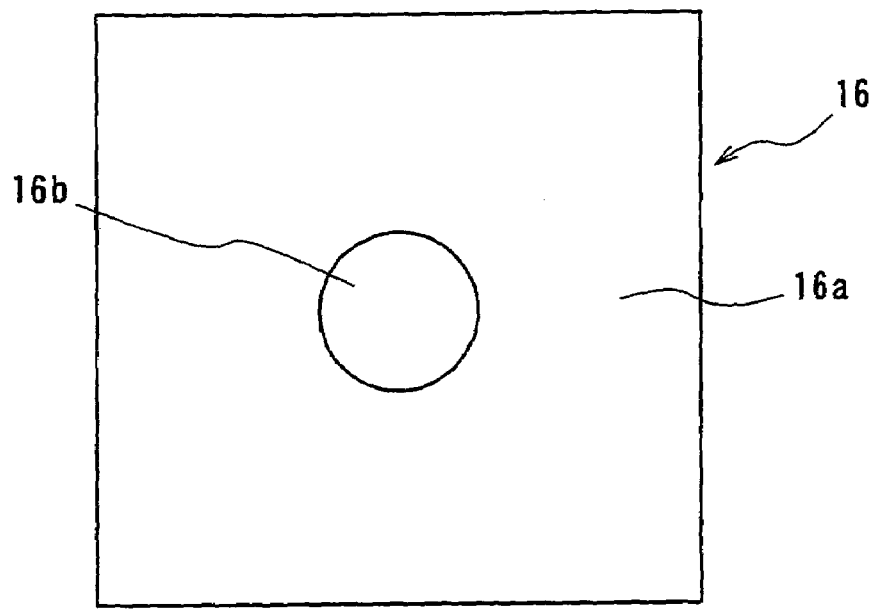
FIGS. 12(a) and 12(b) are, respectively, a planimetric diagram and a cross-sectional view showing the configuration of a phase plate shown in FIG. 11.
Figure 12B:
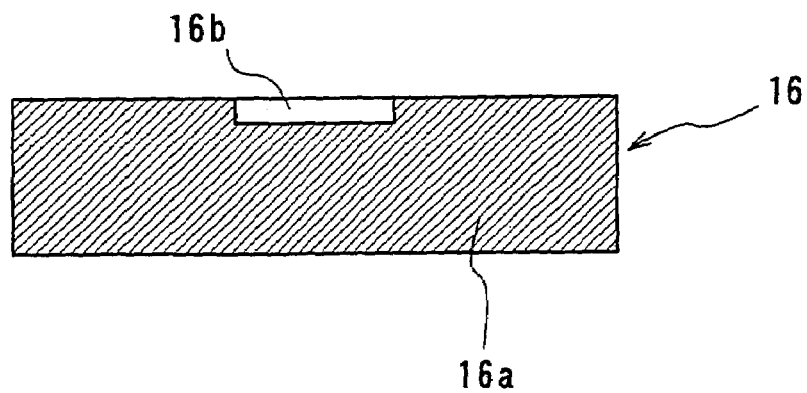
Figure 13:
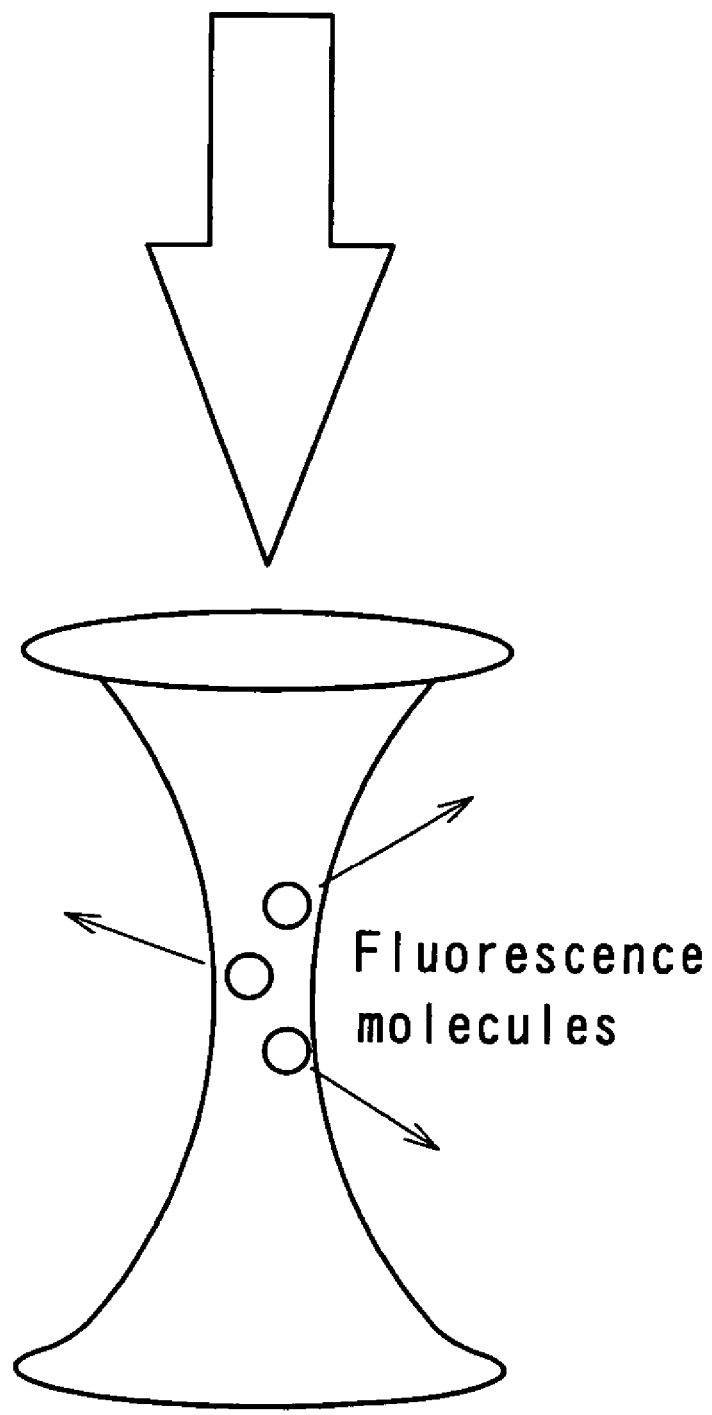
FIG. 13 is a diagram for explaining the principle of the fluorescence correlation method.
Figure 14:
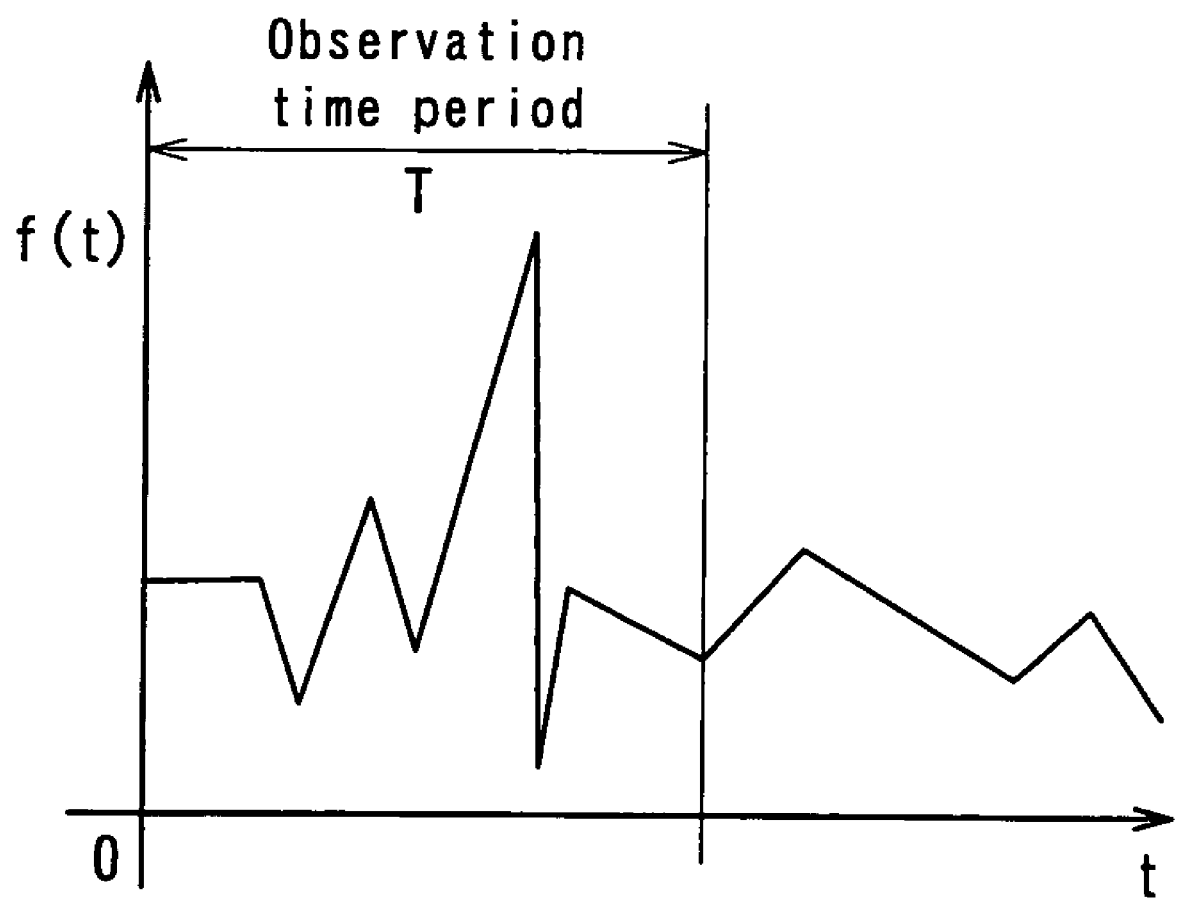
FIG. 14 is a diagram showing an example of fluctuation of a fluorescence intensity in the fluorescence correlation method.
Figure 15:
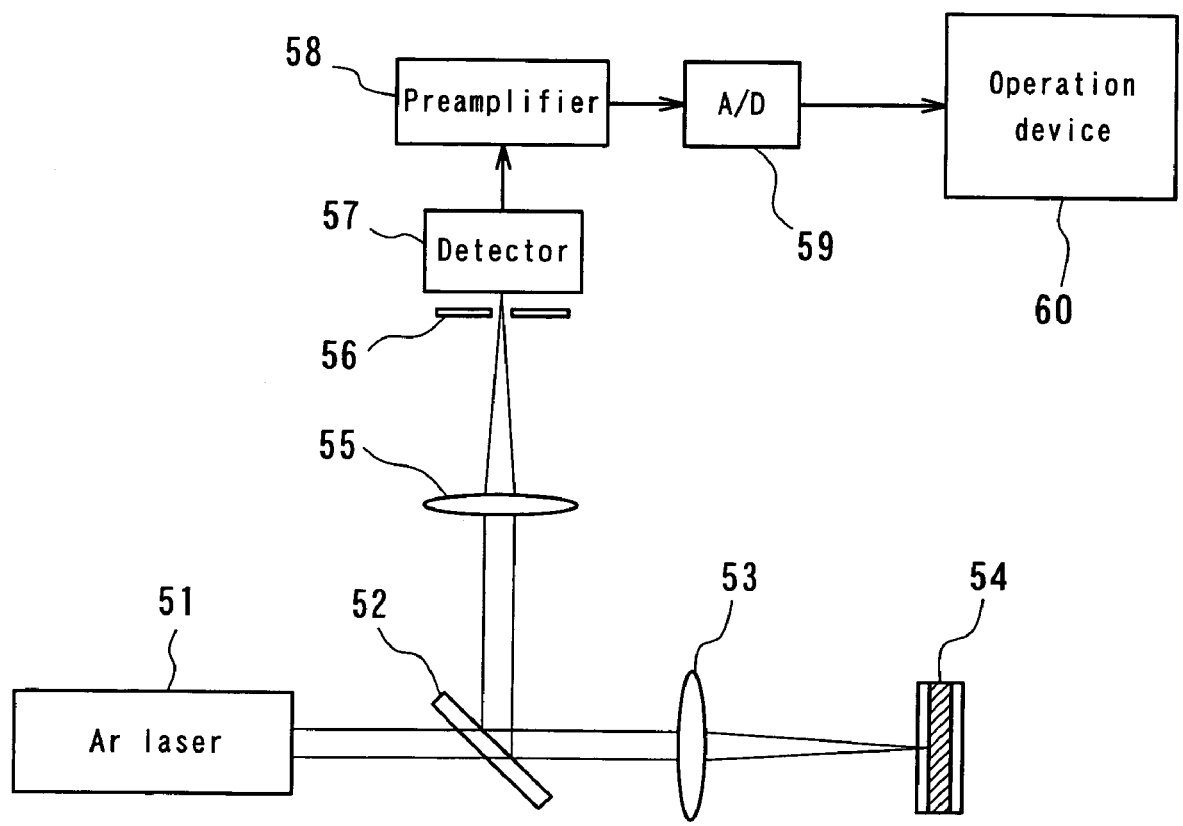
FIG. 15 is a schematic diagram showing a fluorescence correlation analyzing system according to the prior art.

FIG. 11 is a schematic diagram of the three-dimensional analyzing device, where the device mainly comprises four independent units: a beam source unit 10, a scanning unit 20, a microscope unit 30 and an operation unit 40. An example will be explained below with reference to analysis of a biological specimen dyed with rhodamine 6G It has been confirmed that rhodamine 6G has an absorption band near the wavelength 530 nm, in which it is excited from the ground state (S0) to the first electronically-excited state (S1), and a double resonance absorption band within the wavelength range 600 nm to 650 nm, in which it is excited from the first electronically-excited state (S1) to the second electronically-excited state (S2) of higher energy level (see, for example, E. Sahar and D. Treves: IEEE, J. Quantum Electron., QE-13, 692 (1997)).

In the present embodiment, the beam source unit 10 includes a first beam source comprising a LD exciting type mode locked ND:YAG laser 11 as a coherent beam source for generating a pumping beam having a wavelength 532 nm (a second higher harmonic), and a second beam source comprising a continuous oscillation type Kr laser 12 as a coherent beam source for generating an erasing beam having a wavelength 647.1 nm. The beam source unit 10 further includes a rotary ND filter 13 as a first irradiation intensity adjusting means for adjusting the light intensity of the pumping beam, a rotary ND filter 14 as a second irradiation intensity adjusting means for adjusting the intensity of the erasing beam, an iris 15 for adjusting the beam radius of the erasing beam, a phase plate 16 as a spatial phase modulation means for subjecting the erasing beam to a spatial modulation and a beam combiner 17 for coaxially combining the pumping beam and the erasing beam with each other.

In this beam source unit 10, an erasing beam is continuously emitted from the Kr laser 12 to enter the beam combiner 17 via the rotary ND filter 14, the iris 15 and the phase plate 16, while a pumping beam is pulsedly emitted from the LD exciting type mode locked ND:YAG laser 11 to enter the beam combiner 17 via the rotary ND filter 13. The pumping beam and the erasing beam are then coaxially synthesized by the beam combiner 17 and outputted to the scanning unit 20.

The phase plate 16 serves to spatially modulate the erasing beam so that a three-dimensional region without an exposure to the erasing beam is formed in the proximity of the focal point of an objective lens of a microscope unit to be described hereinafter. The phase plate 16 comprises, as exemplarily shown in the plan view of FIG. 12(a) and sectional view of FIG. 12(b), a quartz substrate 16a having a phase distribution region including a circular etching section 16b formed by etching to have a radius of 1.76 mm in radius and a depth of 718 nm. More concretely, the circular etching section 16b is formed by a chemical etching method in which the quartz substrate 16a is corroded to have an optical length difference of $\lambda/2$.

By forming a phase distribution region on the phase plate 16 in this manner, the erasing beam transmitting through the circular etching section 16b comes to have a phase difference $\pi$ with reference to the erasing beam transmitting through the other region, because the refractive index of the quartz substrate 16a is 1.46 for an erasing beam having a wavelength of 647.1 nm. Thus, by concentrating the erasing beam transmitting through the phase plate 16 onto an in vivo specimen dyed with rhodamine 6G, using an objective lens 32 of a microscope unit 30 to be described hereinafter, an erasing beam having a three-dimensional intensity of zero only in the proximity of the focal point can be obtained due to the interference effect, and the fluorescence of rhodamine 6G can be inhibited.

The scanning unit 20 comprises a half mirror 21, galvanometer mirrors 22 and 23 as a two-dimensional scanning means, a projector lens 24, a pinhole 25, notch filters 26 and 27, and a photoelectron multiplier 28 as a photo-receiving means. In the scanning unit 20, the pumping beam and the erasing beam emitted from the beam source unit 10 are transmitted through the half mirror 21, and then outputted to the microscope unit 30 via the galvanometer mirrors 22 and 23. The fluorescence detected at the microscope unit 30 is reflected on the half mirror 21 via the galvanometer mirrors 22 and 23, and subsequently received by the projector lens 24 via the pinhole 25, the notch filters 26 and 27 and the photoelectron multiplier 28.

Here, the pinhole 25 is provided at the confocal point of the objective lens 32 in the microscope unit 30 to be described hereinafter, and functions as a spatial filter. This spatial filter serves to cut any light emitted from outside of the specimen 35 set on the microscope unit 30, for example, a fluorescence or diffused light from an optical system, and to thereby improve the S/N ratio of the measurement and perform the function of optical sectioning as well as the function of selecting a fluorescence emitted only from the specific depth of the specimen 35, i.e., the function of operating tomography by light.

The microscope unit 30 is a normal, so-called fluorescence type microscope comprising a half mirror 31, an objective lens 32, a positioning stage 33 and an eyepiece lens 34. The microscope unit 30 is designed so that the pumping beam and the erasing beam emitted from the scanning unit 20 are reflected on the half mirror 31 to concentrate, through the objective lens 32 included in the concentration optical system, onto a specimen 35 mounted on the positioning stage 34. A fluorescence is thereby emitted from the specimen 35, and reflected on the half mirror 31 through the objective lens 32 and outputted to the scanning unit 20. The fluorescence transmitted through the half mirror 31 is guided to the eyepiece lens 34 that constitutes an observation means.

An operation unit 40 comprises a preamplifier 41, an analog/digital (A/D) converter 42, an operation means in the form of a personal computer (PC) 43, and a timer 44. The operation unit 40 is designed so that a fluorescence intensity signal outputted from a photoelectron multiplier 28 in the scanning unit 20 is amplified with the preamplifier 41 and converted into a digital signal with the A/D converter 42 to be stored in the PC 43. A sampling timing of an A/D conversion with the A/D converter 42 is controlled by the timer 44, based on a pulse oscillation cycle signal of the pumping beam generated by the LD excitation type mode locked ND:YAG laser 11, and a reference clock signal of the PC 43.

In the above configuration, the beam diameter of the erasing beam transmitting through the phase plate 16 is controlled by the iris 15 so that the diameter corresponds to 5 mm which is $2^{1/2}$ times larger than that of the circular etching section 16b, and the optical axis of the erasing beam and the center of the circular etching are 16b are aligned to completely cancel the intensity of the erasing beam at the focal point of the objective lens 32 by means of an interference effect. Thus, when use is made of an immersion lens having a configuration of 5 mm in effective pupil diameter and 1.4 in numerical, for example, it is possible to obtain, in proximity of the focal point, an ultramicroscopic spatial region of a flat spheroidal shape of approximately 460 nm in diameter in the focal plane and approximately 90 nm in the optical axis direction, to which an erasing beam cannot reach, thereby providing a three dimensional spatial resolution. The corresponds to the ultramicroscopic spatial region of a volume $1.0 \times 10^{-14}$ cm$^3$. The intensity of the erasing beam and the pumping beam are optimized by the rotary ND filters 13 and 14, so as to effectively induce the fluorescence inhibition effect and further improve the spatial resolution.

Since an observation region of the fluorescence emitted from a specimen upon irradiation of the pumping beam has a resolution of $0.2\lambda/NA$ in the optical axis direction, the positioning stage 34 is designed to have a precision of not lower than $0.2\lambda/NA$ at least in the optical axis direction. When, for example, an immersion lens having a diameter of 5 mm and a numerical aperture of 1.4 as described above is used as an objective lens 32, the positioning stage 34 is designed to have a precision higher than 90 nm, because the positional resolution in the optical axis direction is approximately 90 nm. To this end, in the present embodiment, the positioning stage 34 comprises a three-dimensional inchworm stage or the like, which uses a piezoelectric element as a driving source, for example. If a piezoelectric element is applied as the driving source in this way, it is possible to realize the positioning precision up to 10 nm with a computerized control using an encoder as well.

In the embodiment described above, the positions of irradiation of the pumping beam and the erasing beam by the objective lens 32 onto the specimen 35 are set to the desired positions with the galvanometer mirrors 22 and 23 and the positioning stage 34. Then, the erasing beam is continuously irradiated by the objective lens 32 onto the specimen 35, and the pumping beam intermittently. The fluorescence intensity signal obtained from the photoelectron multiplier 28 upon irradiation of the pumping beam is amplified by the preamplifier 41 and converted sequentially by the A/D converter 42 into a digital signal, to be stored in the PC 43 in a time-series manner. The fluorescence correlation function $G(\tau)$ is calculated by the PC 43 with the above formula (5) based on the stored fluorescence intensity signal, which is then used to calculate desired physical values such as a molecular weight and a diffusion coefficient.

As explained above, according to the present embodiment, since the fluorescence observation region can be three-dimensionally confined to a ultramicroscopic region, the fluorescence correlation function is accurately calculated and a desired physical value can be analyzed with a high precision, even when the specimen 35 contains concentrated molecules to be measured.

Further, the three-dimensional analyzing device according to the embodiment comprising the galvano-mirrors 22 and 23 can be used as a high resolution microscope for obtaining a two-dimensional fluorescence image of the specimen 35, by two-dimensionally scanning the pumping beam and the erasing beam on the specimen 35 with these galvano-mirrors 23 and 23. Also, by two-dimensionally scanning the pumping beam and the erasing beam while moving the specimen 35 in the optical axis direction in steps with the positioning stage 34, it is possible to obtain a three-dimensional fluorescence image of the specimen 35. In addition, since the fluorescence correlation function at each measuring point of a two-dimensional or three-dimensional fluorescence image can be calculated, a massive improvement in the amount of information can be achieved, as compared with fluorescence microscopes of the prior art.

The present invention is not limited to the above-described embodiment, and various modifications and changes are possible within the scope of the invention. For example, it is possible to provide the phase plate as shown in FIG. 11 with a phase difference of $(2m+1)\pi$ by a deposition method instead of an etching method. When use is made of magnesium fluoride (MgF$_2$) having a refraction index of 1.38 with respect to the wavelength of the erasing beam, it is possible to deposit, onto a glass substrate having a refraction index of 1.46, magnesium fluoride with a thickness of 760 nm to provide a phase difference of $\pi$ corresponding to m=0, or a thickness of 2280 nm to provide a phase difference of $3\pi$ corresponding to m=3. Further, instead of providing the phase plate 17 with a phase distribution region comprising two concentric circular sections as shown in FIG. 7, it is also possible to provide the phase plate 17 with three concentric circular sections, wherein each pair of neighboring sections provides a different phase difference of $(2m+1)\pi$.

Moreover, the spatial phase modulation means is not limited to a phase plate and may comprise a liquid crystal type photo spatial modulator. Alternatively, a spatial modulation means in the form of a deformable mirror may be used to subject an erasing beam to spatial modulation for three-dimensionally confining the observation region.

The present invention is not only applicable to an analysis of a specimen with the fluorescence correlation function, but also effectively applicable to an analysis of a specimen with a correlation function of different types of response light according to a dyeing material to be used, such as phosphorescence for example.

INDUSTRIAL APPLICABILITY

According to the present invention, a first beam and a second beam having different wavelengths are concentrated and irradiated onto a specimen so that the two beams spatially overlap each other at least partly, to thereby three-dimensionally confine a photoactive region in the specimen and calculate a correlation function of a response light emitted from the confined photoactive region for analyzing a desired physical value of the specimen. Therefore, it is possible to accurately calculate the correlation function of the optical response and highly precisely analyze the desired physical value.

The invention claimed is:

1. A three-dimensional analyzing device comprising:
a first beam source for generating a first beam;
a second beam source for generating a second beam having a different wavelength than said first beam;
a spatial modulation unit for subjecting said second beam to a spatial modulation;
an optical system for three-dimensionally confining a photoactive region in a specimen by irradiating said first beam and said second beam, which has been modulated by said spatial modulation unit, so that said first beam spatially overlaps said second beam at least partly and by utilizing a fluorescence inhibition effect caused by the overlapping of the first beam and the second beam; and
a photo acceptance element for receiving a response light emitted from said photoactive region;
wherein said spatial modulation unit comprises a spatial phase modulation unit including a phase distribution region so as to produce a spatially discontinuous phase difference of $(2m+1)\pi$ in said second beam over a radial direction from an optical axis in a pupil of said optical system, where m is an integer.

2. The three-dimensional analyzing device according to claim 1, further comprising an operation unit for analyzing a desired physical value of said specimen by calculating a correlation function of said response light in the time domain, based on an output of said photo acceptance element.

3. The three-dimensional analyzing device according to claim 1, wherein:
said specimen includes a molecule having at least three electronic states including a ground state;
said first beam has a wavelength which makes said molecule transition from the ground state to a first excited state; and
said second beam has a wavelength which makes said molecule transition from the first excited state to a second excited state having a higher energy level.

4. The three-dimensional analyzing device according to claim 3, wherein the wavelength of said second beam is in a wavelength spectrum of an induced emission of said specimen.

5. The three-dimensional analyzing device according to claim 4, wherein the wavelength of said second beam is within a wavelength spectrum effective to inhibit an emission of said response light from the spatial region exposed to both said first and second beams.

6. The three-dimensional analyzing device according to claim 1, wherein said response light is a fluorescence.

7. The three-dimensional analyzing device according to claim 1, further comprising a first irradiation intensity controlling unit and a second irradiation intensity controlling unit for separately controlling intensities of said first and second beams irradiated to said specimen, respectively.

8. The three-dimensional analyzing device according to claim 1, wherein at least said second beam is a coherent beam.

9. The three-dimensional analyzing device according to claim 1, wherein said spatial phase modulation unit comprises a phase plate.

10. The three-dimensional analyzing device according to claim 9, wherein said phase distribution region comprises an optical thin film for producing said phase difference on an optical substrate.

11. The three-dimensional analyzing device according to claim 10, wherein said phase distribution region comprises at least three concentric circular sections, each pair of neighboring sections producing a different phase difference of $(2m+1)\pi$.

12. The three-dimensional analyzing device according to claim 10, wherein said phase distribution region comprises two sections which are shaped as concentric circles.

13. The three-dimensional analyzing device according to claim 12, wherein a radius of a beam flux of said second beam transmitting through said phase plate is $2^{1/2}r$, where r is a radius of an inner section of said two sections.

14. The three-dimensional analyzing device according to claim 13, wherein a center of said inner section corresponds to a center of curvature of the beam flux radius of said second beam.

15. The three-dimensional analyzing device according to claim 9, wherein said phase distribution region comprises an etching section in an optical substrate for producing said phase difference.

16. The three-dimensional analyzing device according to claim 15, wherein said phase distribution region comprises at least three concentric circular sections, each pair of neighboring sections producing a different phase difference of $(2m+1)\pi$.

17. The three-dimensional analyzing device according to claim 15, wherein said phase distribution region comprises two sections which are shaped as concentric circles.

18. The three-dimensional analyzing device according to claim 17, wherein a radius of a beam flux of said second beam transmitting through said phase plate is $2^{1/2}r$, where r is a radius of an inner section of said two sections.

19. The three-dimensional analyzing device according to claim 18, wherein a center of said inner section corresponds to a center of curvature of the beam flux radius of said second beam.

20. The three-dimensional analyzing device according to claim 1, further comprising a positioning mechanism for positioning, with a precision of $0.2\lambda/NA$, a concentration point on said specimen of said first and second beams, where $\lambda$ is a wavelength of said second beam and NA is a numerical aperture of said optical system.

21. The three-dimensional analyzing device according to claim 1, further comprising a two-dimensional scanning unit for two-dimensionally scanning said first and second beams to said specimen in a plane perpendicular to the optical axis of said optical system.

22. The three-dimensional analyzing device according to claim 1, further comprising a stage for moving said specimen in the optical axis direction of said optical system.

23. A three-dimensional analyzing device comprising:
a first beam source for generating a first beam;
a second beam source for generating a second beam having a different wavelength than said first beam;

spatial modulation means for subjecting said second beam to a spatial modulation;

an optical system for three-dimensionally confining a photoactive region in a specimen by irradiating said first beam and said second beam, which has been modulated by said spatial modulation means, so that said first beam spatially overlaps said second beam at least partly and by using a fluorescence inhibition effect caused by the overlapping of the first beam and the second beam; and photo acceptance means for receiving a response light emitted from said photoactive region;

wherein said spatial modulation means comprises spatial phase modulation means including a phase distribution region for producing a spatially discontinuous phase difference of $(2m1)\pi$ in said second beam over a radial direction from an optical axis in a pupil of said optical system, wherein m is an integer.

24. A three-dimensional analyzing device comprising:

a first beam source for generating a first beam;

a second beam source for generating a second beam having a different wavelength than said first beam;

an optical system for three-dimensionally confining a photoactive region in a specimen by irradiating said first beam and said second beam so that said first beam spatially overlaps said second beam at least partly and by utilizing a fluorescence inhibition effect caused by the overlapping of the first beam and the second beam;

a photo acceptance element for receiving a response light emitted from said photoactive region; and a positioning mechanism for positioning, with a precision of $0.2\lambda/NA$, a concentration point on said specimen of said first and second beams, where $\lambda$ is a wavelength of said second beam and NA is a numerical aperture of said optical system.

* * * * *